United States Patent [19]

Cattani

[11] Patent Number: 4,787,846

[45] Date of Patent: Nov. 29, 1988

[54] DEVICE FOR SHUTTING OFF SUCTION GENERATED THROUGH THE SINGLE TUBES OF DENTAL SURGERY EQUIPMENT

[75] Inventor: Augusto Cattani, Parma, Italy

[73] Assignee: Officine Augusto Cattani & C. S.p.A., Italy

[21] Appl. No.: 58,562

[22] Filed: Jun. 5, 1987

[30] Foreign Application Priority Data

Jul. 24, 1986 [IT] Italy .............................. 40076 A/86

[51] Int. Cl.$^4$ ............................................. A61C 17/04
[52] U.S. Cl. ........................................ 433/95; 433/28
[58] Field of Search ...................... 433/95, 28; 604/119

[56] References Cited

U.S. PATENT DOCUMENTS

| | | | |
|---|---|---|---|
| 3,232,578 | 2/1966 | Cousins | 433/95 |
| 3,476,144 | 11/1969 | Krantz | 433/95 |
| 3,645,497 | 2/1972 | Nyboer | 433/95 |
| 4,212,300 | 7/1980 | Meals | 604/119 |
| 4,226,590 | 10/1980 | Hofmann | 433/95 |
| 4,340,368 | 7/1982 | Lococo | 433/28 |

Primary Examiner—John J. Wilson
Attorney, Agent, or Firm—Darby & Darby

[57] ABSTRACT

The invention relates to a device for shutting off suction generated through the single tubes of dental surgery equipment, which comprises a rotary mechanical obturator (5) located in the grip (1) of the suction tube (2) and attached to a pin (3) that engages in a helical groove (6) offered by the holder (4) in which the grip is replaced whenever the tube is not in use. Pin and obturator rotate as one between an open position and a closed position, the obturator being biased permanently toward the open position by a coil spring (7).

6 Claims, 2 Drawing Sheets

DEVICE FOR SHUTTING OFF SUCTION GENERATED THROUGH THE SINGLE TUBES OF DENTAL SURGERY EQUIPMENT

BACKGROUND OF THE INVENTION

The invention relates to a device for shutting off suction generated through the single tubes of dental surgery equipment.

Dental equipment of the type in question, which will generally incorporate two or more suction tubes, is provided with a device by means of which the vacuum pump is stopped when all tubes are idle, and with devices designed to operate o each of the individual tubes in such a way that suction can be shut off through one tube while retaining the facility of generating suction through the remainder.

To this end, the prior art embraces devices that comprise a mechanical obturator located in the grip of the suction tube; such an obturator is operated manually by the user of the equipment, and blocks the air passage through the tube in such a way that suction is shut off. Devices of this type are not widely used, for two main reasons: first, the user is obliged to check that the obturator has in fact closed each time it is operated, and second, there is the strong likelihood that the user will forget to switch off on completion of the treatment, so that the tube is replaced in its holder with the pump still drawing air.

The prior art also embraces automatic devices these have been in use for some time now and are pneumatic in operation, incorporating a diaphragm which, when actuated by a pneumatic control valve on replacement of the grip of a tube in its holder, shuts off the suction through that particular tube. Such automatic devices perform the function required of them admirably, but tend to be complicated from the construction standpoint, and require a somewhat elaborate pneumatic control circuit; also, there are problems connected with cleaning of the diaphragms, which must be kept permanently free of encrustations or corrosive agents in order to function correctly. Moreover, complex constructional requirements will generally dictate a costly and bulky embodiment of the console that normally accommodates the pneumatic shut-off devices for each suction tube.

It is an object of the invention to overcome the above drawbacks, providing a device for shutting off suction through the single tubes of dental surgery equipment that operates automatically on replacement of the grip of the tube in its holder, and is simple and economic from both constructional and servicing standpoints alike.

An advantage afforded by the device according to the invention is that the user can also operate it with ease by hand, and without replacing the grip in its holder.

SUMMARY OF THE INVENTION

The stated object and advantage and others besides, are realized with a device as disclosed and claimed herein.

Such a device is designed for incorporation into a system having at least on tube provided with a hollow grip connected to suction by way of a flexible hose, and a holder provided with at least one opening into which the grip is slotted when the tube is not in use, and is of the type that has an obturator fitted to the grip of the tube and able to assume a closed position, in which the bore of the grip is occluded, and an open position in which at least one passage is left open through the bore.

The device disclosed comprises a pin that projects externally from the grip and is obliged to move as one with the obturator whilst being capable of movement in relation to the grip, a location element forming part of the holder, which engages the pin whenever the grip is slotted into the holder in such a way that the obturator is urged into the closed position; and spring means that impinge upon the obturator in such a way as to urge it permanently toward the open position.

BRIEF DESCRIPTION OF THE DRAWING

The invention will now be described in detail, by way of example, with the aid of the accompanying drawings, in which.

DESCRIPTION OF THE PREFERRED EMBODIMENTS

Figure 1:
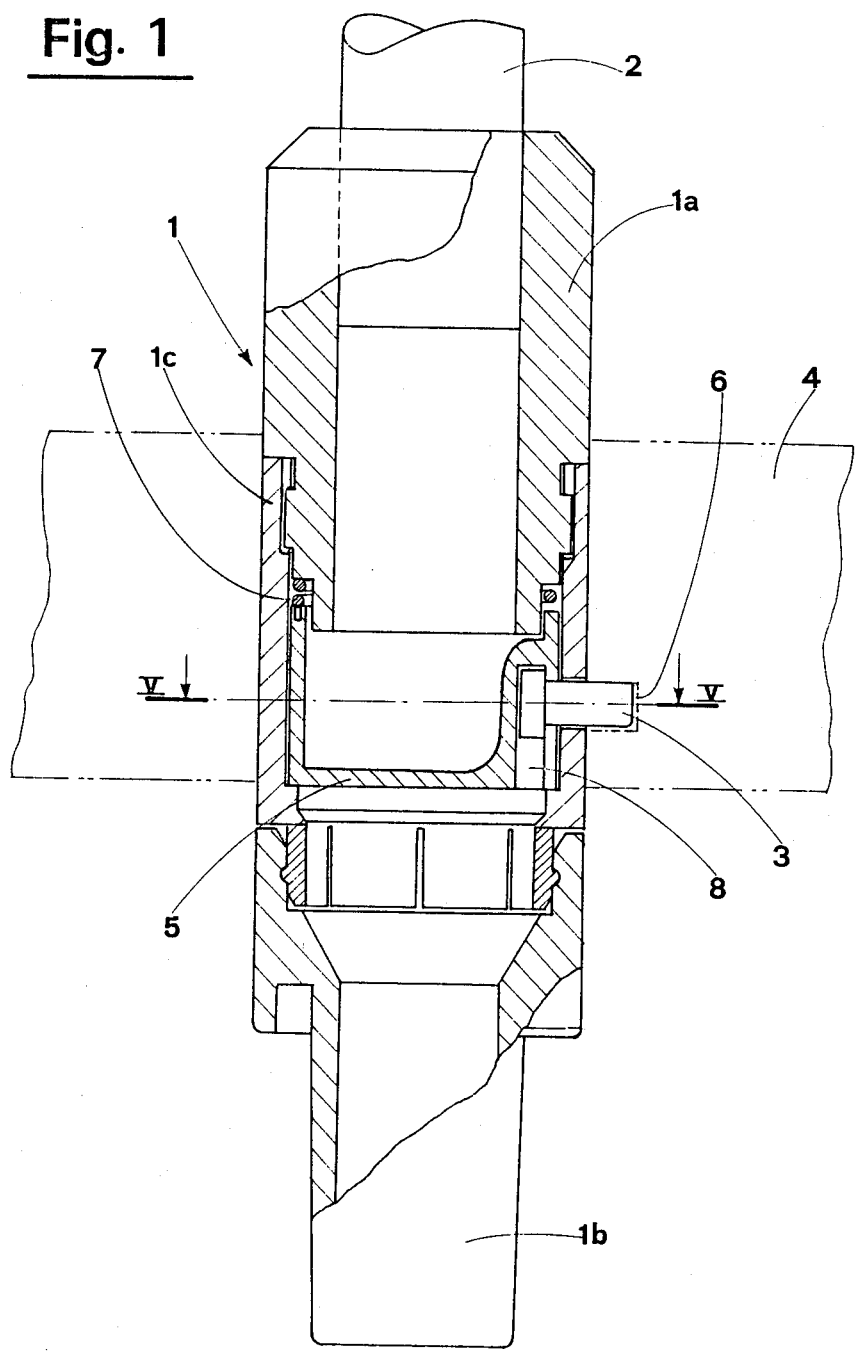
FIG. 1 is a vertical elevation of the grip of the suction tube, illustrated in section.

FIG. 1 provides a sectional view of the hollow grip 1 of a suction tube, which consists in three parts, a top part 1a, a central part 1c and a bottom part 1b; 2 denotes a suction tube fitted to the top part 1a. The bottom part 1b is rotatable in relation to the remainder of the grip, and is attached to a flexible hose (not illustrated) by way of which the entire grip, hence the tube, connects with a vacuum pump (not illustrated).

Figure 2:
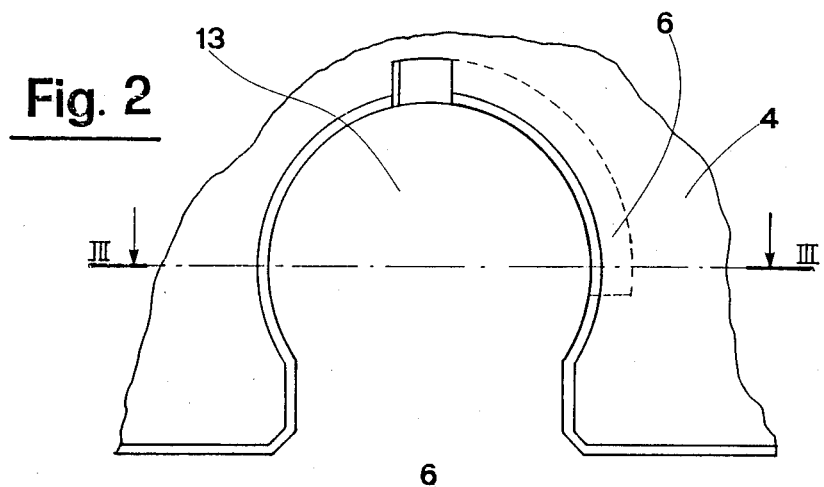
FIG. 2 is a view from above of the opening in the holder that accommodates the grip.
Figure 3:
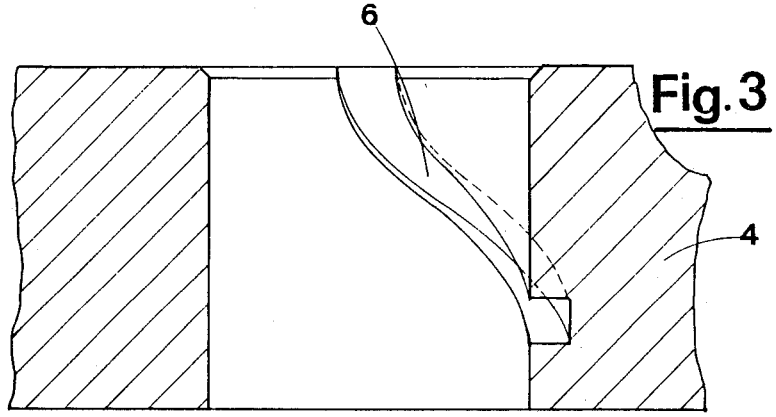
FIG. 3 is the section through III—III in FIG. 2.
Figure 4:
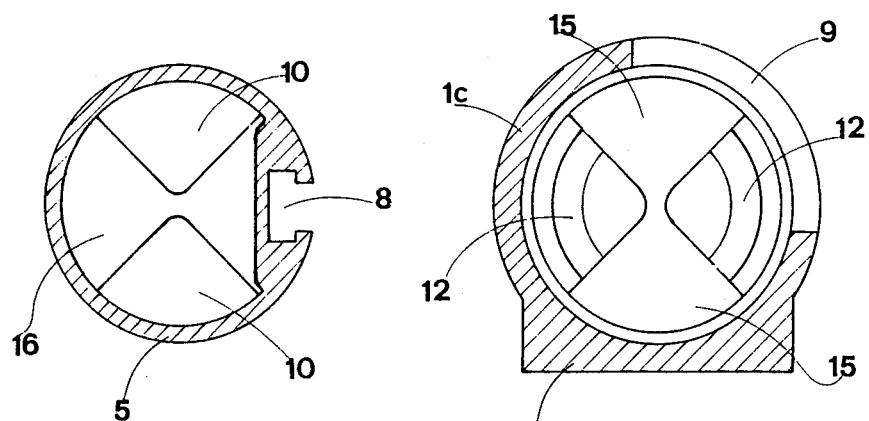
FIG. 4 is a section taken through the obturator coincident with a plane normal to its axis.
Figure 5:
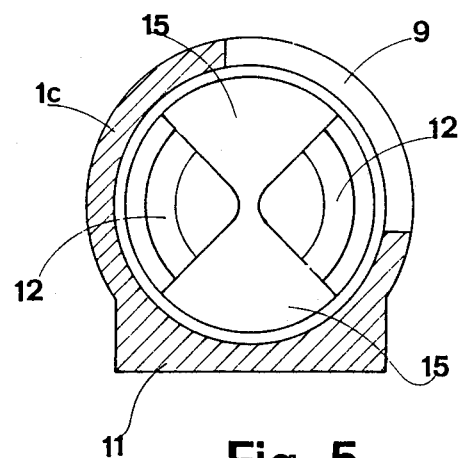
FIG. 5 shows a section of the grip taken through V—V in FIG. 4, from which the obturator is omitted.

FIG. 1 also illustrates a holder 4, visible in part and shown in phantom lines; 13 denotes an opening in the holder (see FIG. 2), into which the grip 1 is slotted when the tube is not in use.

The inside of the grip 1 exhibits an intermediate section that is occluded partly by a horizontal web 15 and provided with two passages 12.

5 denotes an obturator located directly above the intermediate section, coaxial with the grip, which is rotatable about its own axis. The bottom of the obturator 5 is occluded in part by a horizontal web 16 and exhibits two passages 10, whilst the body presents a socket 8 designed to receive one end of pin 3, the end of the pin being embodied such that the pin itself rotates as one with the obturator 5. The pin 3 projects from the grip, externally and at right angles to the grip axis, passing through a circumferential slot 9 that occupies an arc of 90° approx and permits of rotating the pin 3, hence the obturator 5, in relation to the grip. The obturator can thus be rotated between a closed position, in which the passages 12 of the intermediate section are covered by the web 16 and the bore of the grip is occluded, and an open position in which the same passages 12 are substantially in alignment the with the passages 10 of the obturator, and the bore of the grip is left free.

The invention comprises spring means, consisting in a coil spring 7 one end of which is anchored to the body of the grip 1, the remaining end being anchored to the obturator; such spring means serve to urge the obturator permanently toward the open position.

6 denotes a locating element in the holder 4, which is embodied as a helical groove let into the wall of the opening and occupying a right arc of 90° approx. The helical groove 6 offers a cross section by which the pin 3 can be freely accommodated, and the pitch of the helix will be made significantly coarse in order to avoid any impediment to a smooth sliding movement of the pin 3. By way of example, pitch might be maintained constant at three time the diameter of the opening 13 in the holder.

Slotting the grip into the holder, the pin 3 locates in the groove 6, the helical shape of which causes the pin to rotate as the grip descends through the opening 13, thereby moving the obturator into its closed position.

According to the invention, location of the pin 3 in the groove 6 is favored by embodying the opening 13 of the holder non-symmetrically relative to its own axis, and investing the grip with an external cross-sectional profile to match the profile offered by the holder. The grip illustrated in the drawings exhibits a profile that is substantially circular and merges into a polygonal projection 11 at front; accordingly, the opening 13 in the holder 4 is of identical shape.

Embodied thus, the grip must necessarily be offered to the opening 13 at a precise angular position, in relation to its own axis, and location of the pin 3 in the groove 6 is automatic. Faultless location is also ensured by the inclusion of the spring, which keeps the obturator, hence the pin, permanently in a given position.

Operation of the device disclosed is extremely simple. During normal operation—i.e. with the grip remote from the holder, the spring 7 will keep the obturator in the open position, and the user has the immediate advantage of being able to shut off suction momentarily while still holding the grip, by working the pin 3 to rotate the obturator; as soon a the pin 3 is released, the spring 7 returns the obturator to the open position automatically.

Replacing the grip in its holder, interaction of the pin 3 and the groove 6 occasions rotation of the obturator into the closed position, and suction through the tube 2 is shut off; smooth passage of the pin 3 along the length of the helical groove is ensured by the coarse pitch of the helix.

Removing the grip from the holder, the groove 6 and the pin 3 interact to produce the opposite effect of that described above, with the obturator now being rotated into its open position and held there by the action of the spring 7.

The device thus described is markedly simple and economic both from the constructional standpoint and in terms of cleaning and servicing; in particular the top part of the grip is easily separated from the remainder, readily enabling a thorough clean of the inside.

Notwithstanding its simple embodiment, the device performs all the functions that are normally required of a conventional pneumatic valve system automatically; and in addition, the device can be operated manually, instantaneously, by the individual who happens to be making use of the suction tube.

The embodiment of the obturator described in the foregoing and illustrated in the drawings is by no means limitative; for example, a flexible foil type obturator might be adopted, slidably mounted in guides and traversed between an open position and a closed position using the same system of a rigidly connected pin and a location element in the holder. Similarly, the shape and number of the passages and the non-symmetrical external profile of the grip might be other than as described and illustrated.

What is claimed is:

1. A device for closing suction generated through a tube of a dental surgery tool comprising
    a substantially hollow grip having a bore going there through,
    at least one tube being inserted into said grip, said tube connected to suction means,
    a holder having an opening for receiving the grip and a location element,
    an obturator position within an interior of and surrounded by the grip, said obturator is coaxial with the grip, said obturator having a closed position in which the bore of the grip is substantially blocked by the blocking portion and an open position in which at least one passage of the obturator is open,
    a pin projecting externally from the grip, said pin connected to the obturator and movable therewith, said pin movable in relation to the grip.
    said location element engaging the pin when the grip is received by the holder in such a way as to urge the obturator into the closed position,
    spring means provided within the grip and impinging upon the obturator is such a way as to urge the obturator in the open position,
    an interior of said grip having an intermediate section partially blocked by a web portion and having at least one channel going through said inter mediate section, said obturator rotatable about its own axis in such a way that said passage of the obturator coincides with the channel of the intermediate portion in said open position and in said closed position said passage coincides with the web portion of the intermediate section;
    wherein said location element has a helical groove extending across the opening of the holder said groove having a cross-section adopted to slidably receive the pin.

2. A device according to claim 1, wherein the shape of the opening of the holder is non-symmetrical in relation to its own axis, and at least one external section of the grip has the identical shape to the shape of the opening of the holder, so that the grip engages into the opening at a predetermined angular position in relation to its own axis.

3. A device according to claim 3, wherein the grip has at least one external section with a substantially circular configuration and with a polygonal projection at a front portion thereof.

4. A device according to claim 1, wherein said spring means comprises a coil spring having one end anchored to the grip and another end anchored to the obturator.

5. A device for closing suction generated through a tube of a dental surgery tool comprising
    a substantially hollow grip having a bore going there through,
    at least one tube being inserted into said grip, said tube connected to suction means,
    a holder having an opening for receiving the grip and a location element
    an obturator positioned within an interior of and surrounded by the grip, said obturator having a closed position in which the bore of the grip is substantially blocked by the blocking portion and an open position in which at least one passage of the obturator is open, a pin projecting externally from the grip, said pin connected to the obturator and movable therewith, said pin movable in relation to the grip, said location element engaging the pin when the grip is received by the holder in such a way as to urge the obturator into the closed position, spring means positioned within the grip and impinging upon the obturator in such a way as to urge the obturator in the open position.

6. A device according to claim 5 wherein, an interior of said grip having an intermediate section partially blocked by a web portion and having at least one channel going through said intermediate section, said obturator positioned adjacently to and coaxially with the grip, said obturator rotatable about its own axis in such a way that said passage of the obturator coincides with the channel of the intermediate portion in said open position and in said closed position said passage coincides with the web portion of the intermediate section, wherein said location element has a helical groove extending across the opening of the holder, said helical groove having a cross-section adopted to slidably receive the pin.

* * * * *